US00PP19447P3

(12) United States Plant Patent
Pait et al.

(10) Patent No.: US PP19,447 P3
(45) Date of Patent: Nov. 11, 2008

(54) LOBLOLLY PINE TREE NAMED 'CF L3791'

(50) Latin Name: *Pinus taeda*
Varietal Denomination: CF L3791

(75) Inventors: John Pait, Atlanta, GA (US); Plamen Denchev, Victoria (CA); Stephen Attree, Victoria (CA); Robert J. Weir, Cary, NC (US); Andy Benowicz, Victoria (CA)

(73) Assignee: CellFor, Inc., Victoria, BC (CA)

( * ) Notice: Subject to any disclaimer, the term of this patent is extended or adjusted under 35 U.S.C. 154(b) by 0 days.

(21) Appl. No.: 11/635,703

(22) Filed: Dec. 7, 2006

(65) Prior Publication Data

US 2008/0141407 P1 Jun. 12, 2008

(51) Int. Cl.
*A01H 5/00* (2006.01)

(52) U.S. Cl. ..... Plt./213
(58) Field of Classification Search ..... Plt./213
See application file for complete search history.

(56) References Cited

U.S. PATENT DOCUMENTS

2007/0079408 P1 4/2007 Pait et al.

OTHER PUBLICATIONS http://web.org/web/20051130221944/http://www.chesapeakebay.net/info/lobiolly.cfm.*
http://www.cnr.vt.edu/DENDRO/dendrology/syllabus/factsheet.cfm (1 page), Virginia Tech Department of Forestry, College of Natural Resources (2007).
U.S. Appl. No. 11/635,199, Pait et al., Filed Dec. 7, 2006.
U.S. Patent Office Action for U.S. Appl. No. 11/635,199 dated Dec. 12, 2007.

* cited by examiner

*Primary Examiner*—Annette H Para
(74) *Attorney, Agent, or Firm*—Michael Best & Friedrich LLP

(57) ABSTRACT

A new and distinctive variety of a loblolly pine tree which has been denominated varietally as 'CF L3791' which is distinguished by high resistance to fusiform rust and pitch canker, excellent stem straightness, medium to wide crown width, few whorls to medium number of whorls, and very fast growth.

2 Drawing Sheets

Latin name: *Pinus taeda.*
Variety denomination: 'CF L3791'.

BACKGROUND

A new variety of loblolly pine tree (*Pinus taeda*), has been discovered. This selection has been designated as 'CF L3791.'

This new variety is a progeny of two first generation selections. Female parent is a first generation selection made in Williamsburg County, S.C. Male parent is a first generation selection made in Onslow County, N.C.

Cross pollination occurred in early 1997 followed by induction and cryopreservation of embryogenic tissue in 1998. First somatic seedlings were produced in 2000 and planted in early 2001 in seven field experiments. A total of 61 ramets were planted ranging from 5 to 11 ramets per field experiment. The field experiments are located in Mississippi, Florida, Georgia and South Carolina.

BRIEF SUMMARY

A new and distinct cultivar of loblolly pine (*Pinus taeda*) is distinctly characterized by great resistance to fusiform rust and pitch canker, high growth rate, excellent stem straightness, medium to wide crown width, few whorls to medium number of whorls, and which is mature for commercial harvesting sooner than conventionally grown trees under the ecological conditions prevailing in the Piedmont, Atlantic and Gulf Coastal Plains, and Mid-Continent regions of the United States.

The *Pinus taeda* plants of this variety were asexually propagated using an advanced form of micropopagation called somatic embryogenesis carried out at CellFor's production facility in Victoria, Canada. Somatic embryogenesis uses a complex process which relies on the splitting of one embryo into many identical embryos. Somatic embryos can then be grown into plants which are all identical genetically. The asexual propagation occurs at an earlier stage in the plant's life cycle than most other micropropagated plants. The detailed methods for somatic embryogenesis used for asexually propagating conifers in general are described in U.S. Pat. No. 6,372,496 and for loblolly pine in particular in U.S. Patent Application 2004/0203150.

BRIEF DESCRIPTION OF THE DRAWINGS

The drawings are color photographs showing the new variety of loblolly pine.

DETAILED BOTANICAL DESCRIPTION

Figure 1:
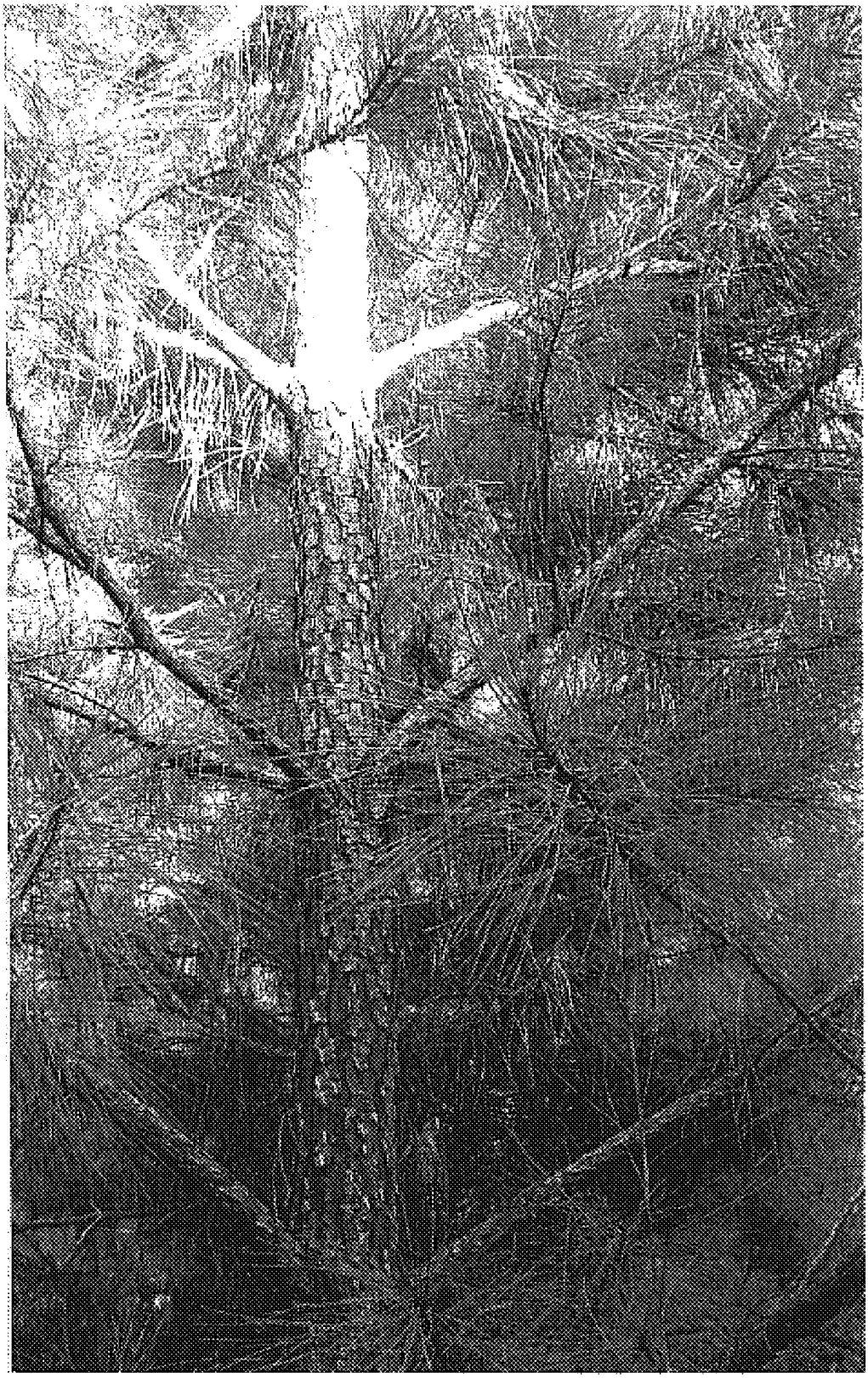
FIG. 1 is a photograph showing 'CF L3791' ramet #7 planted in Holly Hill, S.C. The picture was taken after five field growing seasons. The picture shows excellent stem straightness, few whorls to medium number of whorls per unit stem length, medium angle between the stem and the branches, and medium to large branch diameter (relative to the size of the stem).
Figure 2:
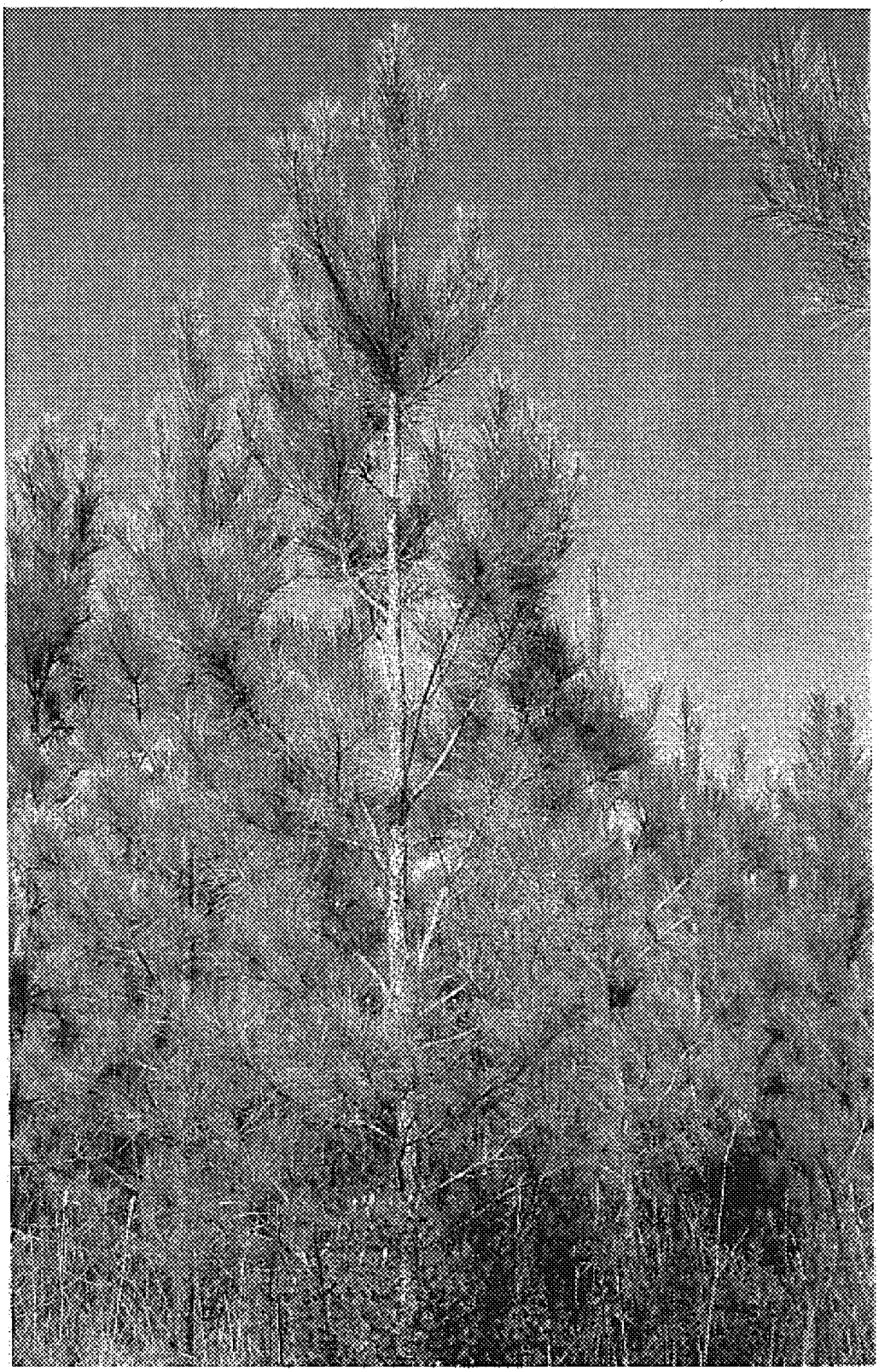
FIG. 2 is a photograph showing 'CF L3791' ramet #4 planted in Winokur, Ga. The picture was taken after five field growing seasons. The picture shows superiority of growth and medium to wide crown width.

The botanical details of this new and distinct variety of loblolly pine tree follow. All color descriptions are made in reference to The Royal Horticultural Society (R.H.S.) Colour Chart (2005).

Parentage: Female parent: (unnamed) first generation selection made in Williamsburg County, S.C. Male parent: (unnamed) first generation selection made in Onslow County, N.C.

Leaf: Evergreen needles, 6 to 9 inches long, with (usually) three yellow-green needles per fascicle. The color of this foliage was measured at age 1 year and age 7 years and was found not to vary significantly with age. The color of the foliage was RHS 137A (30%) and 137C (70%). Diameter of the fascicle was 6/100 of an inch and the average sheath length is 6.75 mm.

Flower: Monoecious; males long cylindrical, red to yellow, in clusters at branch tips; females yellow to purple.

Fruit: Ovoid to cylindrical, 3 to 6 inch red-brown cones; umbo is armed with a short spine, maturing in early fall. Cones are sporadic in 5–7 year old plants.

Branch: Orange-brown in color, fine to moderately stout; buds are narrowly ovoid, light reddish brown.

Bark: Initially red- to gray-brown and scaly; older trees are ridged and furrowed, with somewhat rounded scaly plates; very old trees have red-brown, flat scaly plates. The RHS color is 200C in shade and 187D on exposure to sun.

Shape: A medium to large tree can reach well over 100 feet tall, self-prunes well and develops a fairly straight trunk and an oval, somewhat open crown.

Compared to unimproved loblolly pine trees, 'CF L3791' is characterized by very high growth rate, great resistance to fusiform rust (caused by *Cronartium quercuum* (Berk.) Miyabe ex Shirai f. sp. *fusiforme* (Cumm.) Burds. et Snow), great resistance to pitch canker (caused by *Fusarium circinatum* Nirenburg et O'Donnell), excellent stem straightness, medium to wide crown width, and few whorls to medium number of whorls.

Average height: 26 ft after 5 field growing seasons.

Maximum height: 28 ft after 5 field growing seasons.

Average trunk diameter at breast height (4.5 feet above the soil level): 4.6 inches after 5 field growing seasons.

Maximum trunk diameter at breast height (4.5 feet above the soil level): 6.1 inches after 5 field growing seasons.

Percent stem fusiform rust infection at age 5: 2.

Percent branch fusiform rust infection at age 5: 6.

Percent branch and stem fusiform rust infection at age 5: 0.

Percent dead ramets due to fusiform rust infection at age 5: 0.

Percent stem fusiform rust infection in the USDA Resistance Screening Center (Asheville, N.C.) tests after artificial inoculation with rust sports: 6% (compared to 78% infection in unimproved seedlings).

Percent of seedlings with over 50% of tissue infected by pitch canker in the USDA Resistance Screening Center (Asheville, N.C.) tests after artificial inoculation with pitch canker spores: 0% (compared to 99% infection in unimproved seedlings).

Percent stem straightness gain over unimproved trees: 18.

Propagation: Propagated by somatic embryogenesis.

Seeds: None produced at age 5–7 years of age, plants are not yet mature. Expected seed production by 12–15 years of age.

Use: High yield industrial plantations.

Although the new variety of loblolly pine tree possesses the detailed characteristics noted above as a result of the growing conditions prevailing in the seven test locations, it is to be understood that the variations of the usual magnitude and characteristics incident to changes in growing conditions, irrigation, fertilization, pruning, pest control, climatic variations and the like are to be expected. An example of 'CF L3791' can be found at Plum Creek Oliver year 2001 line trial, Screven county, Ga.

Sampling of branch characteristics: In order to sample branches from a consistent position from one tree to the next the following methodology was utilized. From a point nine feet from the base of the tree, the first complete whorl of limbs below was labeled "Whorl One" and the first complete whorl of limbs above labeled "Whorl Two". This sampling point was chosen because it is the midpoint of the basal sixteen foot log of each tree. A complete whorl was defined as one with at least three branches. An average whorl contained 2–7 branches. All measurements were taken commencing on the South side of the tree and progressing anticlockwise around the stem. When more than three branches were available for measurement on the whorl the largest three branches, by basal diameter, were used for sampling. The following branch characteristics were measured after seven field growing seasons.

Branch diameter: Diameter of each measured branch was taken at its base. Using a caliper the diameter of the branch, over bark, was measured to the closest $100^{th}$ of an inch. 'CF L3791' has an average branch diameter of 1.08 inches at the base of the branch. Zygotic seedlings of the same genetic origin have an average branch diameter of 1.24 inches at the base of the branch.

Branch angle: Utilizing a large protractor, the angle of each branch was measured as its deviation from horizontal. Branch angles were recorded for the portion of the branch emerging from the stem of the tree with data rounded to the closest 10 degrees. 'CF L3791' has an average branch angle of 36.7 degrees from horizontal. Zygotic seedlings of the same genetic origin have an average branch angle of 44.2 degrees from horizontal.

Branch length: The length of each sampled branch was measured directly with a graduated measurement pole. Branch lengths were recorded to the closest 0.5 feet. 'CF L3791' has an average branch length of 8.17 feet. Zygotic seedlings of the same genetic origin have an average branch length of 8.80 feet.

Crown diameter: The width of the crown, at the point where branch measurements were taken, was directly measured with the use of a graduated measurement pole. A radial measurement was taken on the East and West side of each tree. Crown radius was measured to the closest 0.5 feet. Crown width data is presented as diameter of the crown. 'CF L3791' has an average crown diameter of 10.4 feet. Zygotic seedlings of the same genetic origin have an average crown diameter of 10.75 feet.

Internode length: In proximity to the area of the stem utilized for branch measurements the mean internode length was determined for each tree. Internode distances for the calculation of the mean were directly measured from the stem of the tree using a graduated measurement pole. 'CF L3791' has an average internode length of 2.4 feet. Zygotic seedlings of the same genetic origin have an average internode length of 1.7 feet.

Microsatellite markers were used to generate a unique DNA fingerprint for the variety.

Vegetative buds and/or foliar material from eight individuals each produced by controlled crossing among parents for DNA fingerprinting. The DNA extraction protocol of Doyle and Doyle (1987) was used after slight modifications. DNA fingerprinting of parents and their offspring was initially conducted using a set of nine microsatellite markers (Auckland et. al. 2002) and a final set of five primer pairs were selected for the two lines mentioned above (see Table 1, for sequences and conditions of SSR primers) Primer selection was based on their ability to produce unique alleles and the presence of high level of polymorphism.

TABLE 1

Sequences and conditions of the SSR primers currently used in loblolly pine.

| Primer ID | SEQUENCE (5'-3') | LABEL TAIL (F/R); E (end labeled) | $MgCl_2$ (mM) | Tm (° C.) | Size (bp) |
|---|---|---|---|---|---|
| PtTX 2146 | F: CACGACGTTGTAAAAC GACCTGGGGATTTGGATT GGGTATTTG; (SEQ ID NO: 1) R: ATATTTTCCTTGCCCC TTCCAGACA; (SEQ ID NO: 2) | F | 2.5 | 59 | 200 |
| PtTX 3034 | F: CACGACGTTGTAAAAC GACTCAAAATGCAAAAG ACG; (SEQ ID NO: 3) R: ATTAGGACTGGGGATG AT: (SEQ ID NO: 4) | F | 1.5 | 55 | 225 |
| PtTX 3049 | F: GAAGTGATAATGGCAT AGCAAAAT; (SEQ ID NO: 5) R: GCAGACCCGTGAAAGT AATAAACAT; (SEQ ID NO: 6) | R | 3 | 55 | 330 |
| PtTX 3105 | F: TGTCGGTGGAGTTGGC AGTAGACT; (SEQ ID NO: 7) R: GCCCAGCGTTTCCTG; (SEQ ID NO: 8) | E | 2 | 59 | 280 |
| PtTX 3116 | F: CACGACGTTGTAAAAC GACCTCCCAAAGCCTAAA GAAT: (SEQ ID NO: 9) R: CATACAAGGCCTTATC TTACAGAA; (SEQ ID NO: 10) | F | 2.5 | 59 | 165 |

Microsatellite products were detected by M13 tailed primer (Oetting et al., 1995) or infrared dye (IRD)-labeled primer. The amplification products were electrophoresed on 5.5% Long Ranger polyacrylamide gels using a LiCor 4200 automated sequencer (LiCor Inc., Lincoln, Nebr.). For each family, the female and male parents, as well as eight offspring were genotyped.

The observed parental genotypes and their expected offspring's genotypes at five studied SSR loci of each family are presented in Table 2.

TABLE 2

Parental genotypes and their expected offspring's genotypes at five different SSR loci of each family.

| Primer | Genotype Female | Genotype Male | Expected offspring genotype | | | |
|---|---|---|---|---|---|---|
| PtTX 2146 | 199/208 | 190/190 | 190/199 | 190/208 | | |
| PtTX 3105 | 184/190 | 169/169 | 169/184 | 169/190 | | |
| PtTX 3034 | 224/226 | 224/226 | 224/224 | 224/226 | 226/226 | |
| PtTX 3049 | 303/305 | 301/313 | 301/303 | 301/305 | 303/313 | 305/313 |
| PtTX 3116 | 157/163 | 148/151 | 148/157 | 148/163 | 151/157 | 151/163 |

In general, offspring genotypes segregated following expected simple Mendelian segregation (see Table 3, for offspring multi-locus genotypes).

TABLE 3

Parents and offspring genotypes at 5 different SSR loci for two loblolly pine full-sib families.

| | Sample | PtTX 3034[a] | | PtTX 3049[a] | | PtTX 3116 |
|---|---|---|---|---|---|---|
| ID | ID | Allele1 | Allele2 | Allele1 | Allele2 | Allele1 |
| Off-spring | L 3791 | 226 | 226 | 303 | 313 | 151 |

| | Sample | PtTX 3116 | PtTX2146[a] | | PtTX 3105 | |
|---|---|---|---|---|---|---|
| ID | ID | Allele2 | Allele1 | Allele2 | Allele1 | Allele2 |
| Off-spring | L 3791 | 163 | 190 | 199 | 169 | 169 |

[a]Allelic sizes have LiCor primer tails.

References:

Auckland, L., T. Bui, Y. Zhou, M. Shepherd and C. Williams. 2002. Conifer Microsatellite Handbook Corporate Press, Raleigh, N.C., USA.

Doyle, J. J. and J. L. Doyle. 1987. A rapid DNA isolation procedure for small quantities of fresh tissue. Phytochemical bulletin 19:11–15.

Oetting, W. S., H. K. Lee, D. J. Flanders, G. L. Wiesner, T. A. Sellers and R. A. King. 1995. Linkage analysis with multiplexed short tandem repeat polymorphisms using infrared florescence and M13 tailed primers. Genomics 30:450–458.

SEQUENCE LISTING

<160> NUMBER OF SEQ ID NOS: 10

<210> SEQ ID NO 1

-continued

<211> LENGTH: 43
<212> TYPE: DNA
<213> ORGANISM: Artificial
<220> FEATURE:
<223> OTHER INFORMATION: Oligonucleotide PtTX 2146 - F

<400> SEQUENCE: 1 cacgacgttg taaaacgacc tggggatttg gattgggtat ttg 43

<210> SEQ ID NO 2
<211> LENGTH: 25
<212> TYPE: DNA
<213> ORGANISM: Artificial
<220> FEATURE:
<223> OTHER INFORMATION: Oligonucleotide PtTX 2146 - R

<400> SEQUENCE: 2 atattttcct tgccccttcc agaca 25

<210> SEQ ID NO 3
<211> LENGTH: 36
<212> TYPE: DNA
<213> ORGANISM: Artificial
<220> FEATURE:
<223> OTHER INFORMATION: Oligonucleotide PtTX 3034 - F

<400> SEQUENCE: 3 cacgacgttg taaaacgact caaaatgcaa aagacg 36

<210> SEQ ID NO 4
<211> LENGTH: 18
<212> TYPE: DNA
<213> ORGANISM: Artificial
<220> FEATURE:
<223> OTHER INFORMATION: Oligonucleotide PtTX 3034 - R

<400> SEQUENCE: 4 attaggactg gggatgat 18

<210> SEQ ID NO 5
<211> LENGTH: 24
<212> TYPE: DNA
<213> ORGANISM: Artificial
<220> FEATURE:
<223> OTHER INFORMATION: Oligonucleotide PtTX 3049 - F

<400> SEQUENCE: 5 gaagtgataa tggcatagca aaat 24

<210> SEQ ID NO 6
<211> LENGTH: 25
<212> TYPE: DNA
<213> ORGANISM: Artificial
<220> FEATURE:
<223> OTHER INFORMATION: Oligonucleotide PtTX 3049 - R

<400> SEQUENCE: 6 gcagacccgt gaaagtaata aacat 25

<210> SEQ ID NO 7
<211> LENGTH: 24
<212> TYPE: DNA
<213> ORGANISM: Artificial
<220> FEATURE:
<223> OTHER INFORMATION: Oligonucleotide PtTX 3105 - F -continued

```
<400> SEQUENCE: 7

tgtcggtgga gttggcagta gact                                          24


<210> SEQ ID NO 8
<211> LENGTH: 15
<212> TYPE: DNA
<213> ORGANISM: Artificial
<220> FEATURE:
<223> OTHER INFORMATION: Oligonucleotide PtTX  3105 - R

<400> SEQUENCE: 8

gcccagcgtt tcctg                                                    15


<210> SEQ ID NO 9
<211> LENGTH: 38
<212> TYPE: DNA
<213> ORGANISM: Artificial
<220> FEATURE:
<223> OTHER INFORMATION: Oligonucleotide PtTX  3116 - F

<400> SEQUENCE: 9

cacgacgttg taaaacgacc tcccaaagcc taaagaat                           38


<210> SEQ ID NO 10
<211> LENGTH: 24
<212> TYPE: DNA
<213> ORGANISM: Artificial
<220> FEATURE:
<223> OTHER INFORMATION: Oligonucleotide PtTX  3116 - R

<400> SEQUENCE: 10

catacaaggc cttatcttac agaa                                          24
```

We claim:

1. A new and distinct variety of loblolly pine tree named ‘CF L3791’ substantially as described and illustrated.

* * * * *